United States Patent [19]
Chao et al.

[11] 4,322,569
[45] Mar. 30, 1982

[54] CATALYTIC HYDROGENATION OF GLUCOSE TO PRODUCE SORBITOL

[75] Inventors: James C. Chao, West Nyack, N.Y.; Derk T. A. Huibers, Pennington, N.J.

[73] Assignee: Hydrocarbon Research, Inc., Lawrenceville, N.J.

[21] Appl. No.: 174,464

[22] Filed: Aug. 1, 1980

[51] Int. Cl.$^3$ .................. C07C 27/04; C07C 29/14
[52] U.S. Cl. .................................................. 568/863
[58] Field of Search ........................................ 568/863

[56] References Cited

U.S. PATENT DOCUMENTS

| | | | |
|---|---|---|---|
| 1,963,999 | 6/1934 | Larchar | 568/863 |
| 1,990,245 | 2/1935 | Mueller et al. | 568/863 |
| 2,650,941 | 9/1953 | Koome et al. | 568/863 |
| 2,749,371 | 6/1956 | Kasehagen | 568/863 |
| 2,868,847 | 1/1959 | Boyer | 568/863 |
| 2,968,680 | 1/1961 | Kasehagen | 568/863 |
| 3,329,729 | 7/1967 | Brandner et al. | 568/863 |
| 3,538,019 | 11/1970 | Capik et al. | 252/437 |

FOREIGN PATENT DOCUMENTS

| | | | |
|---|---|---|---|
| 582096 | 8/1959 | Canada | 568/863 |
| 6812668 | 3/1970 | Netherlands | 568/863 |

OTHER PUBLICATIONS

Haideggar, "Industrial & Engineering Che.", vol. 7, No. 1, (1968), pp. 107-110.

*Primary Examiner*—Werren B. Lone
*Attorney, Agent, or Firm*—Vincent A. Mallare; Fred A. Wilson

[57] ABSTRACT

Monosaccharides such as glucose solution are catalytically hydrogenated in fixed bed reaction process using a high activity nickel catalyst to produce at least about 98 W % conversion to sorbitol solution. The feedstream pH is controlled to between 7 and 13 by adding a basic solution such as sodium hydroxide. Reaction zone conditions are 500-2000 psig hydrogen partial pressure, 130°-180° C. temperature, and use a ratio of hydrogen gas/feed liquid within the range of 1000-5000. Feedstream liquid space velocity is within range of 0.5-3.5 Vf/Hr/Vc.

10 Claims, 3 Drawing Figures

CATALYTIC HYDROGENATION OF GLUCOSE TO PRODUCE SORBITOL

BACKGROUND OF INVENTION

This invention pertains to the hydrogenation of monosaccharides such as glucose to produce sorbitol product using a continuous fixed bed catalytic process.

Sorbitol is produced commercially from glucose through either electrolytic reduction, or enzymatic, or catalytic hydrogenation processes. Because of economic reasons, the catalytic hydrogenation processes for making sorbitol have been substituted for the other two processes. A batch autoclave process using a Raney nickel pwoder catalyst is presently the major glucose hydrogenation process used in industry. However, batch processes have the disadvantage that new catalyst must be made in situ for each batch of feed. Another drawback of batch processes is that their capacity relative to reaction volume is very small, which causes a need for large storage tanks. Also the consumption of steam and power and labor requirements are relatively high. To overcome these batch process handicaps, a continuous hydrogenation process using a suspended Raney nickel catalyst and two stirred tank reactors in series was developed and is used by some companies, as described by Haideggar in Industrial & Engineering Chemistry, Vol. 7, No. 1, January 1968. However, a disadvantage is the requriement to filter off the catalyst from the product in order to recycle the catalyst, and doing this without reducing the catalyst activity.

It has been further reported by this Haidegger article that VEB Deutsches Hydrierwerk uses a continuous catalytic fixed-bed process for converting glucose to sorbitol at Rodleben, East Germany. The catalyst used is a supported mixed copper/nickel catalyst. However, this process requires a relatively high hydrogen pressure of almost 3000 psig, a low liquid hourly space velocity of 1.0, and a low concentration of glucose in the aqueous feed of 25%, which are deficiencies for the process. It was reported again by Haidegger that local overheating of the catalyst surface due to the heat of the hyrogenation reaction led to isomerization, cracking, and carmel formation. The product sorbitol contained a significant amount of mannitol. Therefore, further process improvements for the catalytic hydrogenation of glucose to produce high conversion to sorbitol product are desired.

SUMMARY OF THE INVENTION

This invention provides an improved continuous fixed bed catalytic process for the hydrogenation of monosaccharides such as glucose to produce high conversion to sorbitol. The process uses moderate reaction conditions and achieves a virtually quantitative conversion of the feed to yield sorbitol product, such as at least about 98 W % conversion. By using a highly active and selective nickel catalyst in a fixed bed reaction zone, and improved process conditions of temperature and liquid space velocity, at least about 98 W % conversion of glucose to sorbitol product is achieved in a continuous fixed-bed reaction process. At higher than optimum space velocities, lower conversions of glucose feed are possible. However, to meet USP and/or FDC specifications for sorbitol, virtually all unconverted glucose has to be removed, which is very costly. Therefore, any process that does not convert glucose to sorbitol in an essentially quantitative manner is not commercially attractive.

The broad hydrogenation reaction conditions required for achieving such high conversion of monosaccharides to sorbitol product are hydrogen partial pressure within range of 500-2000 psig, temperature of 130°-180° C., and feed rate or liquid space velocity in the range of 0.5-3.5 Vf/Hr/Vc (volume feed per hour per volume of catalyst). Also, the feedstream pH must be controlled to between 7 and 13 by adding a basic solution to the feed as needed, such as NaOH, $Ca(OH)_2$, and such. The hydrogen flow rate used is quite important and is related to the liquid feed rate and the quantity of catalyst used, as the hydrogen gas flow provides for carrying the feed liquid droplets through the catalyst bed to achieve intimate contact with the catalyst. The excess hydrogen forms the continuous phase in the reactor, whereas the liquid flows down over the catalyst particles. Local overheating in the bed is avoided by incipient evaporation of water used as the solvent. It has been found that the ratio of hydrogen gas to liquid feed rate at standard conditions should be within the range of about 1000 to 5000 for achieving glucose conversion of at least about 98% by weight to sorbitol product. The conditions of hydrogen partial pressure, temperature, and liquid space velocity are selected as needed to achieve at least about 98 W % conversion of the feed to sorbitol product.

Reaction zone conditions preferred for achieving a high conversion of monosaccharides such as glucose to sorbitol are 750-1600 psig hydrogen partial pressure, 140°-170° C. temperature, 0.6-3.3 V/Hr/V space velocity, hydrogen/liquid feed ratio of 1500-4000, and the preferred glucose conversion is 99-100 W %. The unconsumed hydrogen from the reaction is purified and recirculated through the reaction zone for reuse along with fresh hydrogen as needed.

The catalyst used in the fixed bed reaction zone is a reduced and stabilized nickel on a silica-aluminia support, and usually contains 60-66 W % nickel. A pellet or tablet form catalyst having 1/16-¼ inch diameter is usually preferred because of its greater ease of handling and operation in a fixed bed reactor, and the reaction rate increases with a smaller catalyst size. The fresh catalyst is stabilized by coating it with a mono-molecular layer of carbon dioxide to prevent spontaneous oxidation during reactor charging operations and the catalyst is activated by hydrogen treatment during initial operation. This prevents side reactions and catalyst deactivation during the start-up period.

This process can utilize as feedstock all aldoses including hexoses (monosaccharides) which are convertible into alditols, including glucose, fructose, and mannose, with glucose being the preferred feed for sorbitol manufacture. The glucose feed can be obtained from potatoes, corn, or molasses, with the preferred feed being from potato starch.

The principal advantages of this improved catalytic hydrogenation process for monosaccharides such as glucose to produce sorbitol are:

(a) high conversion (above 98 W %) of glucose to sorbitol, thus making costly glucose separations from the sorbitol product unnecessary (b) use of a fixed bed of stabilized highly active nickel catalyst at process conditions that alleviate local overheating leading to undesirable side reactions, such as isomerization, cracking and carmellization.

(c) less severe or moderate operating conditions, thereby reducing equipment and utility costs, while improving reactor productivity.

DESCRIPTION OF PREFERRED EMBODIMENT

Figure 1:
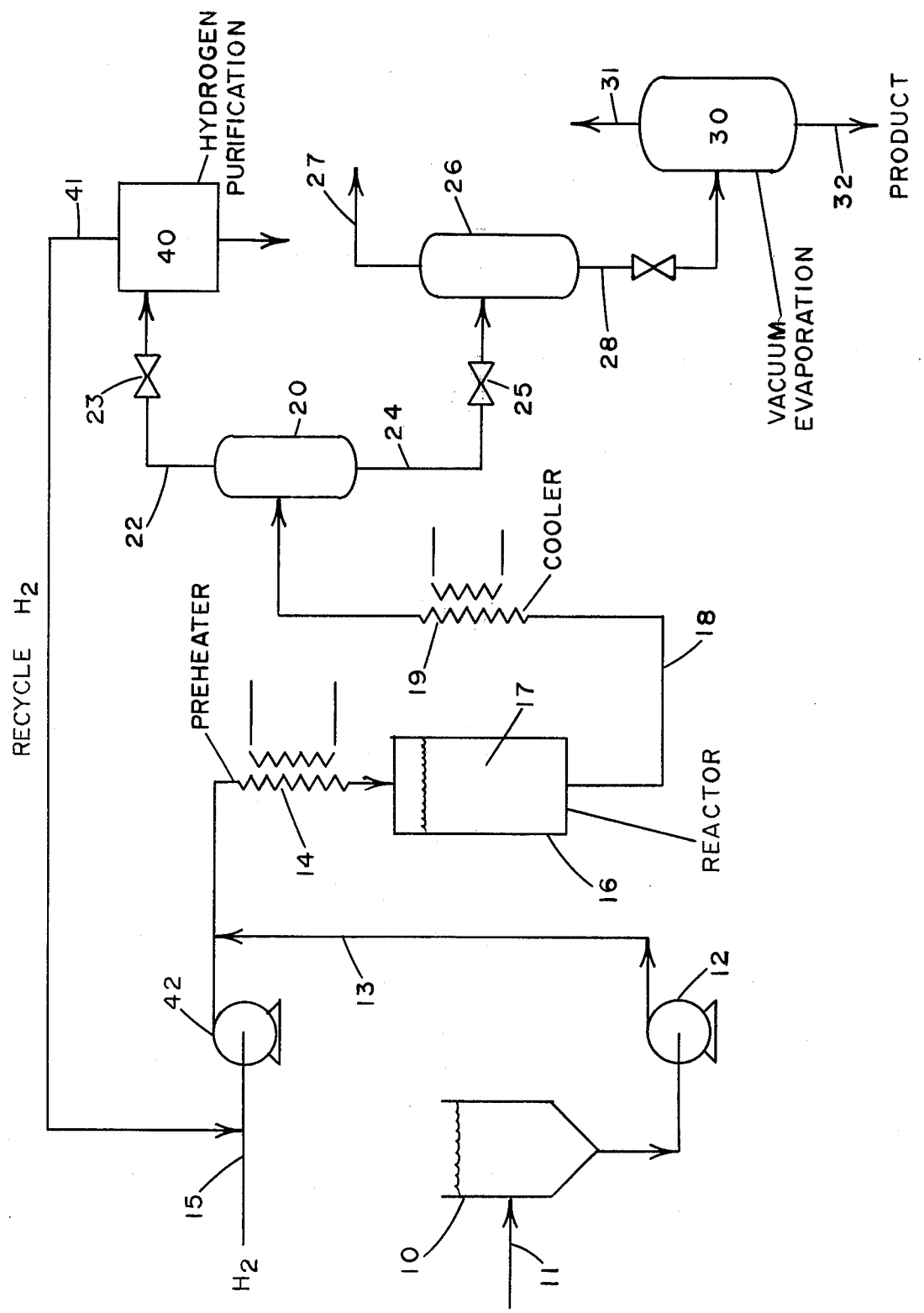
FIG. 1 is a schematic flow diagram of a process for catalytic hydrogenation of glucose feed to produce sorbitol.

As shown in FIG. 1, a 30-50 W % glucose solution in water such as obtained from potato starch is provided at 10 and its pH is adjusted to 7.0-13 preferably by addition of sodium hydroxide at 11. The resulting solution is pumped at 12 through preheater 14 along with make-up hydrogen at 15. After the solution is preheated by any convenient means such as steam to at least about 100° C., it is passed into pressurized reactor 16.

The reactor contains a fixed bed of particulate high activity nickel catalyst 17, and the liquid feed and hydrogen gas are preferably passed downwardly through the bed in intimate contact with the catalyst. The reactor is maintained at elevated hydrogen partial pressure of 500-2000 psig, preferably 750-1600 psig, and temperature conditions of 130°-180° C., preferably 140°-170° C. The glucose solution feed rate or liquid space velocity in the reactor should be at least about 0.5 V/Hr/V, and should usually not exceed about 3.5 V/Hr/V for satisfactory high glucose conversion to sorbitol product. The ratio of hydrogen gas to glucose liquid feed at standard conditions should be at least about 1200 for obtaining at least about 98 W % glucose conversion to sorbitol, and need not exceed about 5000 for achieving near 100% glucose conversion to sorbitol. Hydrogen/liquid feed ratios between about 1500 and 4000 are usually preferred for high conversion operations, along with pH between about 7.5 and 10.5. The glucose is reacted and at least about 98 W % converted to sorbitol solution product. To avoid further costly separations of glucose from the sorbitol product, the preferred conversion is 99-100 W %.

The catalyst used in reactor 16 is a special reduced and stabilized nickel on silica-alumina support catalyst material containing 60-66 W % nickel and used in pellet, tablet or crushed form such as having 4-12 mesh (U.S. Sieve Series) particle size (0.187-0.066 inch). The catalyst has a surface area within the range of about 140 to 180 M$^2$/gm, and becomes more active with use up to a limiting catalyst age. This activity pattern is due to use of a "stabilized" catalyst, which is covered with a monomolecular layer of carbon dioxide to prevent spontaneous oxidation of the highly active nickel when the catalyst is exposed to the air during charging it into the reactor. In industrial practice, the catalyst is usually prereduced in situ by passing hydrogen therethrough to achieve maximum conversion of glucose to sorbitol. Limiting the pretreatment step to about two hours is usually sufficient, since a catalyst with too high an initial activity may cause undesirable carbon deposition on the catalyst.

The reactor effluent stream at 18 is cooled in heat exchanger 19 and passed to high pressure separator 20, wherein the fluid is separated into an overhead gas stream 22 and bottoms liquid stream 24. Overhead stream 22 contains mainly hydrogen and is passed through pressure-control valve 23 to hydrogen purification step 40. The purified hydrogen stream 41 having at least about 75% purity is recycled through compressor 42 to preheater 14 for reuse in the reactor.

Separator bottoms liquid stream 24 is pressure-reduced at 25 and passed to low pressure receiver 26, from which overhead stream 27 is withdrawn as a gas product stream containing $H_2$, and trace amounts of $CH_4$. Liquid stream 28 is withdrawn to provide the high percentage sorbitol product in water solution.

Excess water can be removed from stream 28 by vacuum evaporation at 30 to provide a more concentrated sorbitol liquid product 32, with the water vapor being vented at 31. The vacuum pressure used is usually in the range of 50-80 mm. mercury. Because of the high percentage conversion of glucose to sorbitol achieved by this process, recycling of a portion of the sorbitol solution 28 to the reactor 18 for increased conversion or glucose/sorbitol separation steps are unnecessary.

Figure 2:
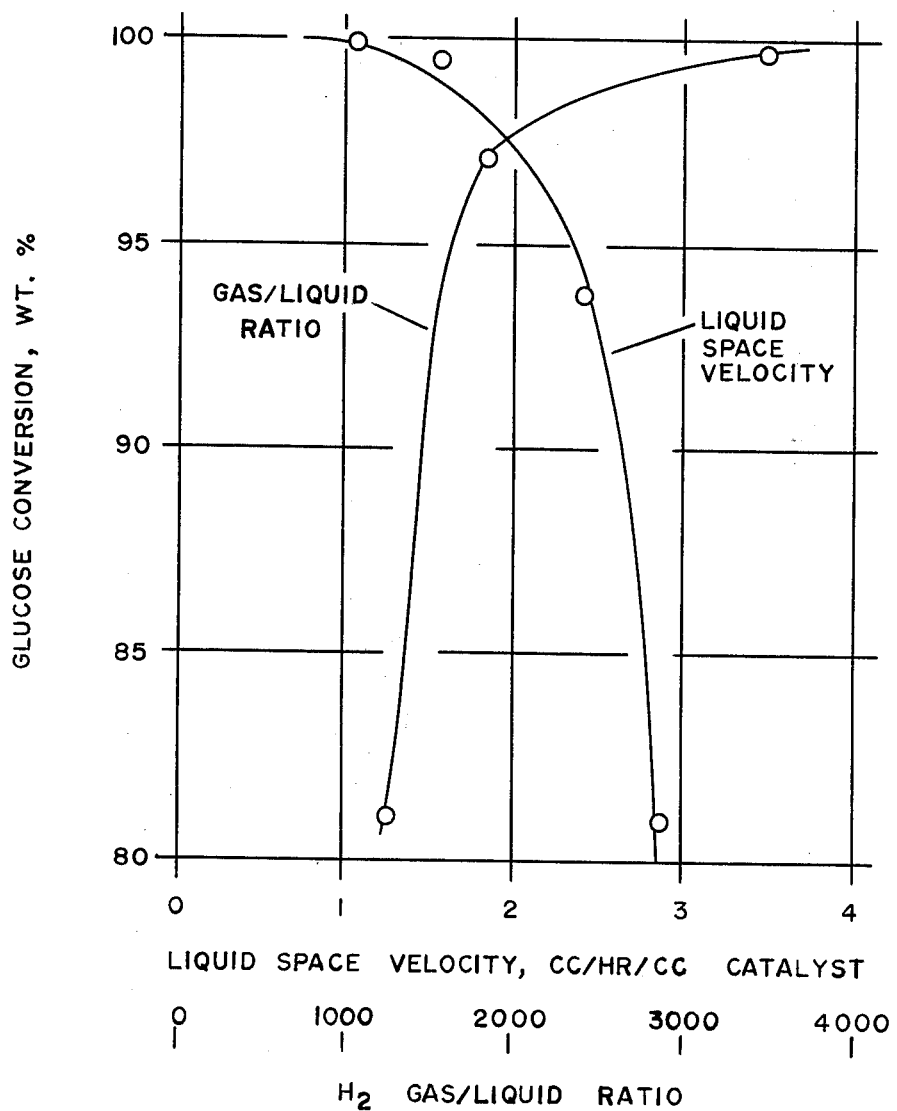
FIG. 2 is a graph of percent glucose conversion vs. liquid space velocity and hydrogen/liquid feed ratio used.

Typical effects on glucose conversion of feed liquid space velocity and hydrogen gas/feed lliquid ratio at 1000 psig hydrogen partial pressure and 145° C. temperature are presented in FIG. 2. It is noted that a significant reduction in percent glucose conversion occurs at liquid space velocities greater than about 2.5 V/Hr/V, and for hydrogen gas/liquid feed ratios less than about 1800. Higher conversions of glucose can be achieved at higher liquid space velocities and at lower gas/liquid ratios if either the reaction temperature or hydrogen partial pressure or both are increased. Higher pressures, however, would require a more costly reactor, and higher temperatures are limited to about 170° C. to prevent undesired side reactions.

This invention is further illustrated by the following examples, which should not be construed as limiting the scope of the invention.

EXAMPLES

Monohydrate dextrose, also known as D-(+)-glucose, obtained from J. T. Baker Chemical Company, was diluted with distilled water to make 40 W % solution. Sodium hydroxide was added as needed to adjust the pH value of the glucose solution to 8. The glucose was then mixed with hydrogen, heated and introduced into a fixed-bed reactor system suitable for glucose hydrogenation. The process steps used were very similar to the schematic diagram shown in FIG. 1. The downflow reactor was fabricated from stainless steel pipe, 0.464 inch inside diameter by 12 inch long, and provided a volume of 33 cc. The bottom portion of the reactor was filled with 20 cc of 8-12 mesh (U.S. Sieve Series) nickel catalyst pellets, type Ni-5124T, obtained from Harshaw Chemical Company, and the top portion was filled with 8-12 mesh size tabular alumina which served as the preheating and distribution section for the feed. The reactor was equipped with a three-point thermocouple to monitor the temperature at the top, middle and bottom of the catalyst bed.

Glucose conversion operations were conducted using a range of reactor operating conditions based on previous experience. A gas chromatograph equipped with a hydrogen-flame ionization detector and an integrator was used for samplw analysis, and a "sugar" analysis was done on all the samples. In this analysis, the TMS (trimethyl silylation) method was used. A weighed 1 cc sample was dried and dissolved in 4 cc of anhydrous pyridine. This solution was mixed with 1 cc of BSTFA (bis [trimethylsilyl] trifluoroacetamide) plus 10% TMCS (trimethylchlorosilane) and shaken vigorously for about 30 seconds. Then another 25 cc of pyridine was added. After 10 minutes, one microliter of the solution was injected into a ⅛ inch diameter ×6 ft. long stainless steel gas chromotograph column, filled with 80-100 mesh size 3% OV-17 column packing material, obtained from Supelco, Bellefonte, PA. The temperatures were set at 160° C. for the column and 300° C. for the injector and interface. The helium flow rate was 30 cc/min; pressure of air, helium and hydrogen was 50, 100 and 20 psig, respectively.

Figure 3:
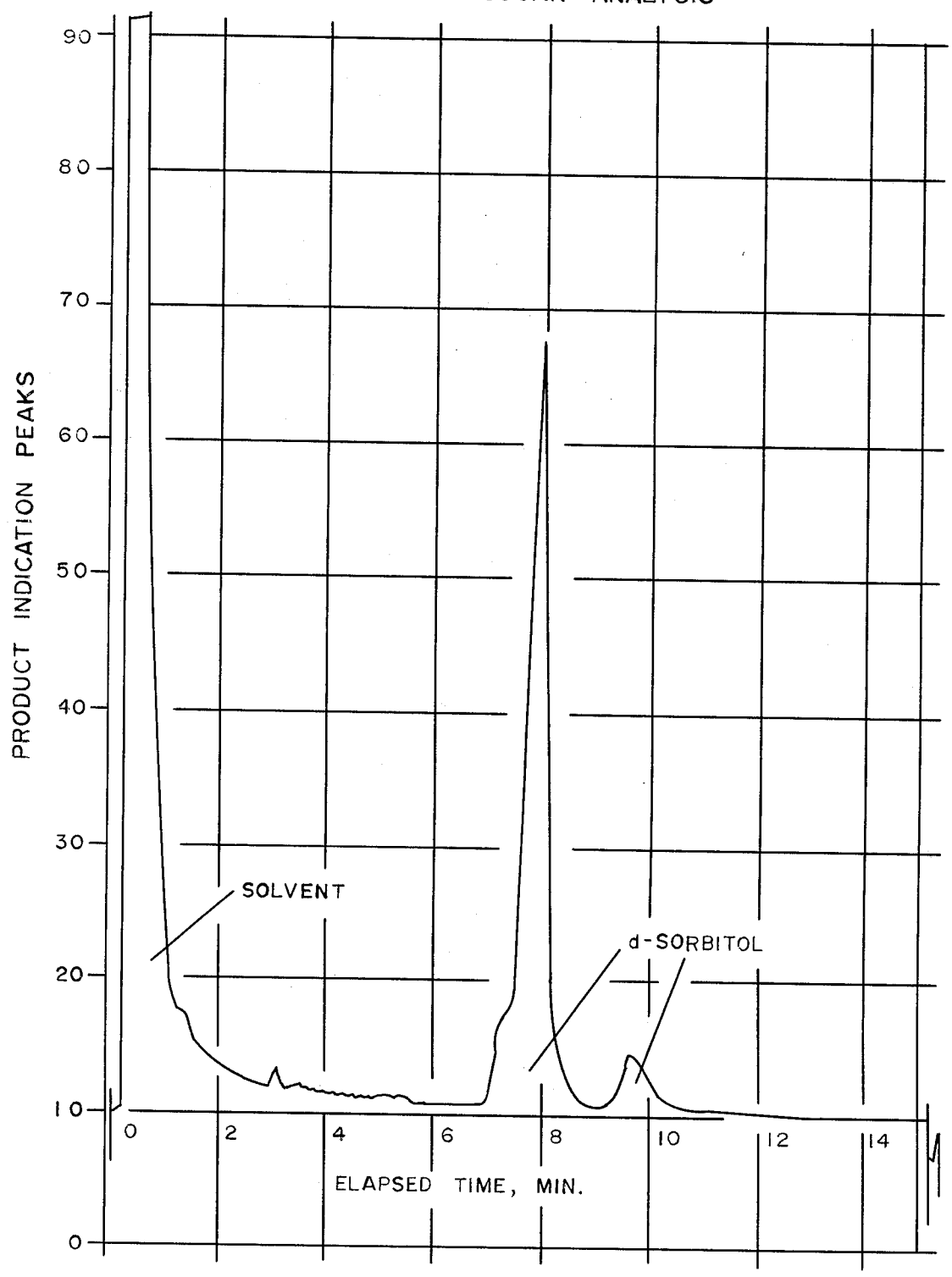
FIG. 3 shows gas chromatograph analysis of sorbitol product obtained.

Typical reaction conditions and results for conversion of 40% glucose solution to sorbitol are shown in the table below for runs A-D inclusive. As shown by the FIG. 3 gas chromatograph analysis chart, only d-sorbitol was detected in the product solutions. Results shown for run E are projected from the data.

|  | Run A | Run B | Run C | Run D | Run E |
|---|---|---|---|---|---|
| H₂ Partial Pressure, psig | 750 | 750 | 990 | 1295 | 1455 |
| Reactor Midpoint Temperature, °C. | 130 | 145 | 145 | 145 | 170 |
| Space Velocity of Liquid Feed, cc/hr/cc catalyst | 1.58 | 1.58 | 1.07 | 1.58 | 3.22 |
| Ratio H₂ Gas/Liquid Feed | 2258 | 2258 | 3335 | 2258 | 2258 |
| Glucose Conversion, W % | 80.5 | 93.2 | 99.6 | 99.9 | 99.9 |

These data show that by proper choice of combination of the operating variable, virtually quantitative conversion of dextrose to sorbitol can be achieved at economically attractive conditions.

Although this invention has been described in terms of the accompanying drawing and preferred embodiment, it will be appreciated by those skilled in the art that many modifications and adaptations of the basic process are possible within the spirit and scope of the invention, which is defined soley by the following claims.

We claim:

1. A process for producing sorbitol by catalytic conversion of monosaccharides, comprising the steps of:
   (a) providing a feedstream containing at least about 20 W % monosaccharide solution and having pH of 7 to 13;
   (b) preheaing the feed and hydrogen gas to at least about 100° C., and passing the heated feedstream mixture through a fixed bed catalytic reaction zone containing a high activity nickel catalyst;
   maintaining the reaction zone at conditions of 500-2000 psig partial pressure of hydrogen, 130°-180° C. temperature, and 0.5-3.5 V/Hr/V space velocity, for achieving at least about 98 W % conversion of the feed; and
   (d) withdrawing product containing substantially sorbitol in water solution.

2. The process of claim 1, wherein the ratio of hydrogen gas to liquid feed at standard conditions is between about 1000 and 5000.

3. The process of claim 1, wherein the catalyst is a stabilized high activity nickel on silica-alumina support containing 60-66 W % nickel and having 1/16-¼ in. dia. particle size and surface area of 140-180 M²/gm.

4. The process of claim 1, wherein the reaction zone conditions are maintained at 750-1600 psig partial pressure of hydrogen, 140°-170° C. temperature, and 0.6-3.3 V/Hr/V space velocity.

5. The process of claim 1, wherein the pH of the feedstream is controlled within range of 7.5 to 10.5 by adding sodium hydroxide.

6. The process of claim 1, wherein the feed is 30-60 W % glucose solution in water and the glucose conversion is 98.5-99.9 W % to sorbitol in water solution.

7. The process of claim 6, wherein the feedstream is potato glucose.

8. A process for producing sorbitol by catalytic conversion of monosaccharides, comprising the steps of:
   (a) providing a feedstream containing about 20-60 W % monosaccharide solution and having pH of 7.5 to 10.5;
   (b) preheating the feed and hydrogen gas to about 100°-120° C., and passing the heated feedstream mixture through a fixed bed catalytic reaction zone containing a high activity nickel catalyst containing 60-66 W % nickel on silica-alumina support and having particle size within range of 1/16-¼ inch;
   (c) maintaining the reaction zone at conditions of 750-1600 psig partial pressure of hydrogen, 140°-170° C. temperature, and 0.6-2.6 V/Hr/V space velocity, and hydrogen gas/liquid feed ratio of 1200-4000 at standard conditions for achieving at least about 98 W % conversion of the feed; and withdrawing product containing substantially sorbitol in water solution.

9. A process for making alditol by catalytic conversion of the corresponding aldose, comprising the steps of:
   (a) providing a feedstream containing at least about 20 W % alditol solution and having pH of 7 to 13;
   (b) preheating the feed and hydrogen gas to at least about 100° C., and passing the heated feedstream mixture through a fixed bed catalytic reaction zone containing a high activity nickel catalyst containing 60-66 W % nickel on silica-alumina support;
   (c) maintaining the reaction zone at conditions of 500-2000 psig partial pressure of hydrogen, at 130°-180° C. temperature, and 0.5-3.5 V/Hr/V space velocity, for achieving at least about 98 W % conversion of the feed; and
   (d) withdrawing product containing alditol in water solution.

10. The processs of claim 9, wherein the feedstream is mannose 20-50 W % solution and the product is mannitol.

* * * * *